United States Patent [19]
Cohen

[11] Patent Number: 5,201,751
[45] Date of Patent: Apr. 13, 1993

[54] ACUPUNCTURE NEEDLE FOR MIXED USE

[76] Inventor: Andre Cohen, 65, Avenue General Leclerc, Nimes, France, 30 000

[21] Appl. No.: 585,783

[22] Filed: Sep. 20, 1990

[51] Int. Cl.⁵ .............................................. A61B 17/34
[52] U.S. Cl. ..................... 606/189; 604/204
[58] Field of Search .............. 606/189, 204; 604/216, 604/217, 204

[56] References Cited

U.S. PATENT DOCUMENTS

| | | | |
|---|---|---|---|
| 798,093 | 8/1905 | Dean | 604/204 |
| 2,642,064 | 6/1953 | Lawshe | 604/204 |
| 2,667,165 | 1/1954 | Smith | 604/216 |
| 2,935,067 | 5/1960 | Bouet | 604/216 |
| 3,861,392 | 1/1975 | Moen | 606/189 |
| 3,905,375 | 9/1975 | Toyama | 206/365 |
| 3,976,078 | 8/1976 | Toriella | 606/189 |
| 4,013,073 | 3/1977 | Cunningham | 604/204 |
| 4,018,222 | 4/1977 | McAleer et al. | 604/204 |
| 4,479,496 | 10/1984 | Hsu | 606/189 |
| 4,883,473 | 11/1989 | Thomas | 604/217 |
| 4,955,871 | 9/1990 | Thomas | 604/217 |

FOREIGN PATENT DOCUMENTS

| | | | |
|---|---|---|---|
| 3501204 | 7/1986 | Fed. Rep. of Germany | 606/189 |
| 2635003 | 2/1990 | France | 606/189 |

Primary Examiner—C. Fred Rosenbaum
Assistant Examiner—William Lewis
Attorney, Agent, or Firm—Jacobson, Price, Holman & Stern

[57] ABSTRACT

An acupuncture needle-tank apparatus for mix use comprising a needle of the type used in acupuncture, provided with an internal channel constituting a cannula suitable to let pass a liquid or viscous product therethrough, connected to a tank without piston, containing said product, wherein the cannula has an external diameter under 0.3 mm and the tank being of an external diameter under 15 mm. The tank is further characterized in that it is of a material deformable by simple finger pressure to allow the flow of the product it contains.

7 Claims, 1 Drawing Sheet

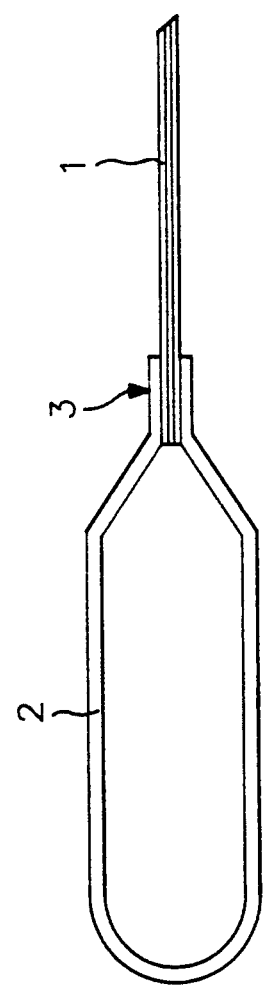

ACUPUNCTURE NEEDLE FOR MIXED USE

BACKGROUND OF THE INVENTION

1. Field of the Invention

This invention relates to a device designed to supply any convenient product, for example a medicine, including a tank connected to a needle provided with an internal bore or axial passage.

2. Description of the Prior Art

Known devices of the type involved are as follows:

1) syringe-types including a large diameter (over 0.3 mm) bored needle connected to a large-sized tank with a piston used in medicine injections ( e.g. homeopathic substances, vitamins, trace elements) or in aesthetical surgery (e.g. collagen) which provoke pain and practical inconvenients (e.g. skin tugging, dose difficult to miniaturize) linked to the needle dimensions and to the tank weight;

2) the types described in U.S. Pat. No. 4,508,119 (K. Tukamoto) concerning either a needle of the type used in acupuncture, in special alloy, previously magnetized and having been submitted to the action of an electrostatic field, or a current injection needle, also pre-magnetized and having been submitted to an electrostatic field, used to supply a medicine product previously magnetized in a magnetic box.

In both cases the needles and the tanks are large-sized.

BRIEF SUMMARY OF THE INVENTION

This invention was conceived in order to solve the above problems comprising a bored-needle tank set perfectly meeting the requirements of acupuncture, microinjection medicine and aesthetical microsurgery, i.e. prepared for a mixed use.

A needle of the type used in acupuncture (diameter under 0.3 mm), provided with an internal bore so as to constitute a cannula is connected to a tank of an external diameter under 15 mm and of a short length. It is possible: a) to use the needles in acupuncture and then in therapeutical microinjection during same session; b) to use the device in therapeutical microinjection or in aesthetical microsurgery.

The proposed device is in addition easy to handle, not bulky and rather nontraumatic as much for the tissues as for the tolerance for the patient.

Other features of the invention and the advantages thereof will become apparent from the detailed description below.

BRIEF DESCRIPTION OF THE DRAWING

The invention will now be described in detail with reference to the accompanying drawing.

FIG. 1 is a longitudinal cross-section of an embodiment of the bored-needle tank set.

DETAILED DESCRIPTION

With reference to FIG. 1 the device of this invention includes:

a) a needle 1, of the type used in acupuncture of an external diameter from about 0.15 to about 0.3 mm and of a length form about 3 to about 30 mm (not limitative), using several metals namely iron, molybdenum, cold hammered steel, stainless or Japanese steel, provided internally and lengthwise with an internal bore so constituting a cannula suitable to let a liquid or viscous product pass;

b) a tank 2, without piston, located at one end of the cannula, containing said product of a material deformable by simple finger pressure (plastic, etc) of an external diameter under 15 mm of namely about 5 mm, of a length ranging for example from 20 to 30 mm, eventually coated partially or wholly, with a material (spiral wire for example) that reinforces its structure or makes its griping easy.

The linkage of needle and tank can be obtained by simple plug assemblage of the two pieces, the coupling between cannula and tank provided by the adjusting pressure that results from the external diameter of the needle being larger that the internal diameter of the mouthpiece 3 of the tank within which its end is lodged.

It is to be understood that the mean to lock the cannula and the tank could be of the types generally used for the syringes, the tank could have any convenient shape and it could be exchanged during the session.

I claim:

1. An apparatus for acupuncture treatment and injection of a treating substance in two successive steps, comprising:

a tank having an external diameter less than 15 mm, a mouthpiece at one end, and designed to contain said treating substance; and an acupuncture needle having a distal end, a proximal end, and an axial passage therethrough communicating with said tank for conducting said treating substance which complements the energetics action of the puncture of the needle, wherein said proximal end of said acupuncture needle is axially and lengthwise connected to said mouthpiece of said tank.

2. The apparatus as claimed in claim 1, wherein said tank is made of a material deformable by simple finger pressure.

3. The apparatus as claimed in claim 1, wherein said acupuncture needle has an external diameter less than 0.3 mm.

4. An apparatus for acupuncture treatment and injection of a treating substance in two successive steps, comprising:

a tank having a mouthpiece at one end and designed to contain said treating substance;

a coating material covering at least part of said tank for reinforcing said tank; and an acupuncture needle having a distal end, a proximal end, and an axial passage therethrough communicating with said tank for conducting said treating substance which complements the energetics action of the puncture of the needle, wherein said proximal end of said acupuncture needle is axially and lengthwise connected to said mouthpiece of said tank.

5. The apparatus as claimed in claim 4, wherein said tank is entirely coated with said coating material.

6. An apparatus for acupuncture treatment and injection of a treating substance in two successive steps, comprising:

a tank having a mouthpiece at one end and designed to contain said treating substance;

a gripping material covering at least part of said tank for improving gripping of said tank by the user; and an acupuncture needle having a distal end, a proximal end, and an axial passage therethrough communicating with said tank for conducting said treating substance which complements the energetics action of the puncture of the needle, wherein said proximal end of said acupuncture needle is axially and lengthwise connected to said mouthpiece of said tank.

7. The apparatus as claimed in claim 6, wherein said tank is entirely coated with said gripping material.

* * * * *